United States Patent [19]

Höhlein et al.

[11] 4,431,751

[45] Feb. 14, 1984

[54] METHOD AND APPARATUS FOR PRODUCING SUPERHEATED STEAM WITH THE HEAT OF CATALYTIC METHANIZATION OF A SYNTHESIS GAS CONTAINING CARBON MONOXIDE, CARBON DIOXIDE AND HYDROGEN

[75] Inventors: Bernd Höhlein, Jülich; Manfred Vorwerk, Erkelenz; Udo Boltendahl, Havetoft, all of Fed. Rep. of Germany

[73] Assignee: Kernforschungsanlage Jülich GmbH, Jülich, Fed. Rep. of Germany

[21] Appl. No.: 382,211

[22] Filed: May 26, 1982

[30] Foreign Application Priority Data

Jun. 3, 1981 [DE] Fed. Rep. of Germany ....... 3121991

[51] Int. Cl.$^3$ .............................................. C07C 1/04
[52] U.S. Cl. ................................ 518/706; 48/197 R; 122/4 D; 518/712; 422/190
[58] Field of Search ...................... 518/706, 705, 712; 48/197 R; 122/4 D

[56] References Cited

U.S. PATENT DOCUMENTS

| | | | |
|---|---|---|---|
| 3,870,738 | 3/1975 | Yamamoto et al. | 518/706 |
| 4,205,961 | 6/1980 | Möller et al. | 518/726 |
| 4,294,932 | 10/1981 | Lohmuller et al. | 518/706 |
| 4,298,694 | 11/1981 | Skov | 518/706 |

OTHER PUBLICATIONS

B. Höhlein, "Methanisierungsvetfahren unter besonderer Berücksichtigung der Arbeiten zum NFE-Projekt", Berichte der Kernforschungsanlage Jülich, Jül—1589, May 1979.
"High-temp methanation tests run", by H. Harms.
"High Temperature Methanation in the Long-Distance Nuclear Energy Transport System", B. Höhlein et al, May 11, 1981.

Primary Examiner—Howard T. Mars
Attorney, Agent, or Firm—Frishauf, Holtz, Goodman & Woodward

[57] ABSTRACT

Only a part of the synthesis gas supply is passed through a first internally cooled catalytic reactor (1) and the hotter gas coming out of it is reunited with the remaining gas supply for passing through an adiabatic reactor (2) that is followed by a heat exchanger (3) on its way to a second internally cooled reactor (4) in which the methanization reaction is completed. Water is heated up to practically the saturated steam temperature in the cooling system of the last mentioned reactor and is converted to saturated steam in the cooling system of the first internally cooled reactor. The saturated steam is superheated in the above-mentioned heat exchanger. To make the process run more smoothly a steam drum is provided through which the hot water piping between the cooling systems of the two internally cooled reactors runs and the saturated steam is brought into the steam drum and from it to the heat exchanger before it is superheated. Additional heat exchangers are used for first preheating of the water and for two stages of preheating the synthesis gas. Adjustments of the proportion of the synthesis gas that goes through the first internally cooled reactor makes possible a control that assures that the outlet temperature of the adiabatic reactor will not exceed a safety limit required for the stability of the catalyst. No mechanical propulsion, nor compression, of the gas is necessary at any stage, nor any recycling, nor introduction of steam for control of the process.

5 Claims, 2 Drawing Figures

|  | a | b | c | d | e | f |
|---|---|---|---|---|---|---|
| $H_2O$ | 0,0 | 0,409 | 0,250 | 0,349 | 0,414 | 0,0 |
| $CH_4$ | 0,171 | 0,563 | 0,424 | 0,517 | 0,567 | 0,968 |
| $CO$ | 0,110 | 0,0 | 0,026 | 0,002 | 0,0 | 0,0 |
| $CO_2$ | 0,077 | 0,006 | 0,044 | 0,026 | 0,004 | 0,006 |
| $H_2$ | 0,640 | 0,022 | 0,255 | 0,106 | 0,015 | 0,025 |
| $N_2$ | 0,0 | 0,0 | 0,0 | 0,0 | 0,0 | 0,0 |

FIG. 2

METHOD AND APPARATUS FOR PRODUCING SUPERHEATED STEAM WITH THE HEAT OF CATALYTIC METHANIZATION OF A SYNTHESIS GAS CONTAINING CARBON MONOXIDE, CARBON DIOXIDE AND HYDROGEN

This invention concerns a process and apparatus for utilizing the heat of the catalytic methanization of a synthesis gas containing carbon monoxide, carbon dioxide and hydrogen for producing superheated steam that can be used, for example, for electric power generation, or for other purposes, while a useful gas with a high methane content is being produced at the same time.

Particularly the invention concerns a process in which a part of the synthesis gas is first passed through at least one first internally cooled reactor in which saturated steam is formed and then reunited with the remaining synthesis gas for passing successivley through an adiabatic reactor, a heat exchanger in which the saturated steam is superheated and a second internally cooled reactor which also serves to preheat the water prior to its conversion to steam.

The conversion of a synthesis gas containing carbon monoxide, carbon dioxide and hydrogen into a gas containing methane, since it takes place exothermally, is useful as a source of energy. Synthesis gasses of this kind are readily produced with supply of heat (and particularly with the utilizatof nuclear energy) by the decomposition of a gas containing hydrocarbons, where at least a part of the decomposition gas products are supplied to a consumption device as an energy carrier. In this connection, compare German published patent application DE-AS No. 16 01 001. In the consumption device the conversion of the synthesis gas takes place and useful heat is taken out for external use. For the decomposition of hydrocarbon-containing gases methane and higher molecular weight hydrocarbons such as ethane, propane and butane are particularly suitable.

It is known to carry out the conversion of the synthesis gases in adiabatic and/or internally-cooled reactors. In adiabatic reactors the removal of heat takes place in heat exchangers connected downstream of the reactor whereas in internally cooled reactors the heat is directly withdrawn from the catalytic process. For steam generation the internally cooled reactors have cooling systems through which water flows, which are disposed within the catalyst bed. When adiabatic reactors are brought into the operation of the process a maximum permissible operating temperature for the catalyst must be taken into account which may not be exceeded if the catalyst material is to remain stable. It is known to control the operating temperature by recycling a part of the gas flowing out of the adiabatic reactor and mixing it with the synthesis gas or by the introduction of water vapor into the synthesis gas. Whereas with recycling of gas additional circulation equipment is made necessary, particularly in the form of compressors, in the case of the introduction of steam the basic economy of the process is reduced.

In carrying out the process with internally-cooled reactors, the passage of heat between catalyst bed and the cooling medium is above all to be taken into account. The advantage of the internally cooled reactor is the possibility to obtain an extensive methanization by corresponding cooling of the gas without subjecting the catalyst to impermissibly high temperature.

It is known to methanize synthesis gas in installations which contain internally-cooled reactors along with adiabatic reactors, in which connection one may compare the publication of B. HÖHLEIN, "Methanisierungsvetfahren unter besonderer Berücksichtigung der Arbeiten zum NFE-Projekt", Berichte der Kernforschungsanlage Jülich, JüL—1589, May 1979. Such installations allow operation of the process without recirculation of the gas by means of the usually trouble-prone compressors. It is known from DE-OS No. 29 49 588 to lead synthesis gas through an adiabatic reactor followed by a heat exchanger and then into an internally-cooled reactor in order to generate superheated steam. In that case the saturated steam is generated in the internally cooled reactor and then superheated in the heat exchanger.

SUMMARY OF THE INVENTION

It is an object of the invention to make the methanization of synthesis gas more economic and to obtain an optimization of the steam generation in the process by extensive utilization of the heat quantities extractable from the catalytic conversion.

Briefly, the water from which steam is produced is first heated up in the last or second internally cooled reactor to approximately the saturated steam temperature and then is converted into saturated steam in the first internally cooled reactor or reactors through which a portion of the synthesis gas flows, and the saturated steam is thereafter superheated in a heat exchanger which is heated by the full flow of gas coming out of at least one adiabatic reactor on its way to the second internally cooled reactor, the adiabatic reactor being fed with the synthesis gas with which the portion drawn off to operate the first internally-cooled reactor has been reunited. Thus, the water, which is essentially water suitable for boiler feed prepared, if necessary, in the usual way, flows through the cooling system of the two internally cooled reactors one after the other, but only a part of the synthesis gas passes through the one or more first internally cooled reactor or reactors in order to deliver essentially the vaporization heat to the cooling water for the formation of saturated steam.

A mass balance between the cooling systems of the internally cooled reactors is further supported and promoted in an elaboration of the invention by which a steam drum is provided through which the steam formed in the first internally cooled reactor or reactors is introduced and from which the steam then proceeds to the heat exchanger for superheating while the hot water line connecting the water outlet of the second internally cooled reactor passes through the water jacket of the steam drum on its way to the cooling water inlet of the one or more first internally cooled reactors. The steam drum serves to provide a smooth and evenly proceeding operation of the process.

The heat still contained in the product gas that flows out of the last internally cooled reactor is advantageously utilized in two additional heat exchangers, preferably operated in parallel, respectively for the first preheating of the water and of the synthesis gas. Further preheating of the synthesis gas is preferably also provided by still another heat exchanger through which the hot gas supplied to the second internally cooled reactor flows after coming out of the first-mentioned heat exchanger in which the steam is superheated before being furnished for use elsewhere.

The apparatus of the invention follows closely the pattern of the process steps. There are arrayed in the flow direction of the synthesis gas at least one first internally cooled reactor, then at least one adiabatic reactor followed by a heat exchanger and then a second internally cooled reactor. The first internally cooled reactor is connected on a branch of the synthesis gas line so that only a portion of the synthesis gas flow passes through this reactor and a valve is provided for controlling the magnitude of that portion, preferably interposed in the line through which the gas that does not go through the one or more first internally cooled reactors passes. The branch rejoins the line leading to the adiabatic reactor and then to the heat exchanger that closely follows the adiabatic reactor. The cooling systems of the two internally cooled reactors are connected in succession in such a way that in the second internally cooled reactor the fresh water, which may already have been preheated somewhat as already mentioned, is heated up and saturated steam is then generated after the water reaches the cooling system of the first internally cooled reactor. The steam drum above-mentioned has its tubing interposed in the hot water line between the cooling system of the internally cooled reactors and is supplied with water heated to near the saturated steam temperature in the second internally cooled reactor. The input of the cooling system of the first internally-cooled reactor or reactors is connected to receive hot water from the steam drum for conversion into saturated steam and the output of the cooling system of the first internally cooled reactor is connected to the steam drum to lead the saturated steam to the steam chamber of the steam drum, from which the saturated steam flows to the heat exchanger the hot of which follows the adiabatic reactor, for superheating so that the steam exits from the system in a superheated state.

As already mentioned, additional heat exchangers are preferably provided in the installation for the first preheating of the fresh water and of the synthesis gas by means of heat from the product gas and also another for further preheating of the synthesis gas by the hot gas flowing to the second internally cooled reactor from the first-mentioned heat exchanger that superheats the steam.

BRIEF DESCRIPTION OF THE DRAWINGS

The invention is further described by way of illustrative example by reference to the annexed drawings, in which FIG. 2 is a tabulation of the composition of the gas at different places in the installation to provide a comprehensive view of the progress of the methanization reaction.

DESCRIPTION OF THE ILLUSTRATED EMBODIMENT

Figure 1:
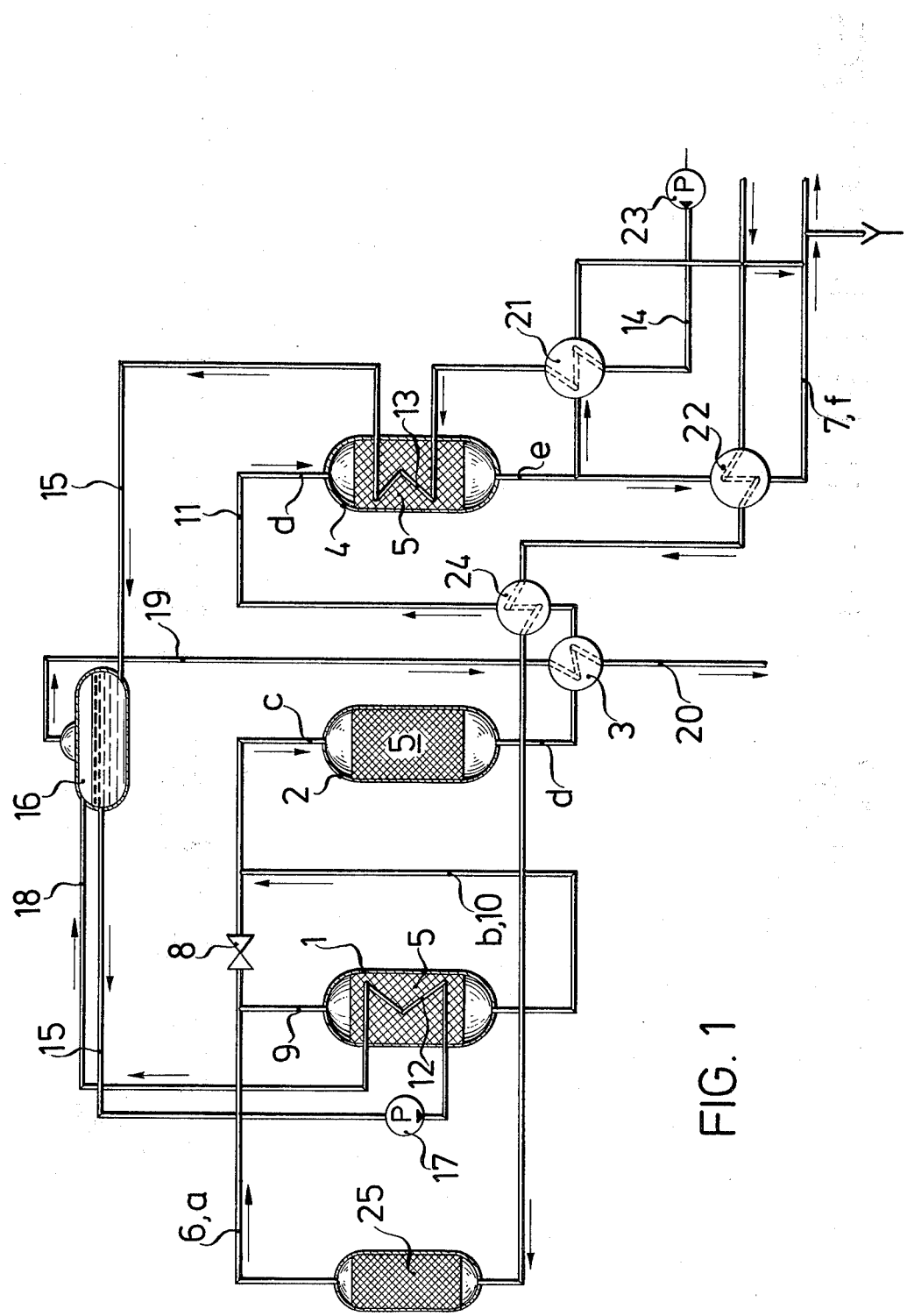
FIG. 1 is a diagram of apparatus according to the invention for practicing the process of the invention with the use of one first and one second internally-cooled reactor and a single adiabatic reactor.

As can be seen in FIG. 1 the installation for the practice of the process comprises a first internally cooled reactor 1, an adiabatic reactor 2 which is followed by a heat exchanger 3 and a second internally cooled reactor 4. All reactors are provided with a catalyst filling over or through which the gas can be passed for chemical conversion. As the synthesis gas there is used a gas containing at least 50% by volume of hydrogen and, 10% by volume of carbon monoxide and carbon dioxide. As catalysts a nickel-containing catalyst bed 5 is utilized. In the illustrated example, as appears in FIG. 2, a synthesis gas flows to the reactors over a gas line 6 containing substantially 17% by volume $CH_4$, 11% by volume CO, 8% by volume $CO_2$ and 64% by volume $H_2$, with the remaining volume being nitrogen and possibly small amounts of higher molecular weight hydrocarbons.

The composition of the input gas is given in column a of the tabular presentation in FIG. 2. In the presence of the catalyst in the various reactors it is converted to a methane-rich product gas having about 97% by volume $CH_4$ and a remainder volume of a few percent consisting of carbon dioxide, hydrogen and nitrogen (column f in FIG. 2) and is then supplied through a product gas line out of the installation for use elsewhere.

The first internally cooled reactor, the reactor 1, is connected to the synthesis gas line 6 by means of a branch line 9 and a portion of the synthesis gas is thereby caused to flow through the reactor and from the outlet of the reactor 1 through a return branch line 10 into the gas supply line for reunification with the remainder of the synthesis gas before reaching the inlet of the adiabatic reactor 2. From the adiabatic reactor 2 the gas is led by means of a connecting line 11 through the heat exchanger 3 to the second internally cooled reactor 4. In the two internally cooled reactors 1 and 4 the cooling systems 12 and 13 are respectively disposed within the catalyst beds. A fresh water supply 14 is connected to the inlet of the cooling system 13 of the second internally cooled reactor 4. A hot water line 15 leads from the outlet of the cooling system 13 to the inlet of the cooling system 12 of the first internally-cooled reactor 1. A steam drum 16 is connected into the hot water line 15 and the hot water proceeding out of the steam drum 16 is fed by means of a pump 17 to the cooling system 12 of the first internally cooled reactor 1. At the steam drum 16 there discharges a saturated steam line 18 connected at its other end to the outlet of the cooling system 12 of the first internally cooled reactor 1. There is also connected to the steam drum 16 a saturated steam supply line 19 in which the saturated steam is brought to the heat exchanger 3 for superheating. The superheated water vapor then flows from the output of the heat exchanger 3 through a steam line 20, for example to steam turbines driving generators for generating electrical energy. The last named aggregates of equipment are not shown in the drawing.

The fresh water supplied to the cooling system of the second internally cooled reactor 4 is heated in the reactor 4 practically to saturated steam temperature. In the cooling system 12 of the first internally cooled reactor, there accordingly takes place the conversion of the hot water, taken from the steam drum 16 by means of the pump 17, into saturated steam. The portion of the synthesis gas that flows through the first internally cooled reactor 1 is so adjusted (by means of the valve 8) that the recombined gas flows at the input of the adiabatic reactor 2 will have a temperature in the temperature range between 250° and 350° C. and so that at the output of the adiabatic reactor a temperature of between 600° and 700° C. is reached. In the illustrated example the entrance temperature in the first internally cooled reactor is 330° C. at a pressure of 40 bar, the entrance temperature at the adiabatic reactor is 325° C. at 39 bar and the outlet temperature of the adiabatic reactor is 675° C.

at 38.5 bar. The gas enters into the heat exchanger 3 at the last-given temperature and superheats the saturated steam flowing through the heat exchanger after coming from the steam drum 16. The second internally cooled reactor 4 is set to operate at a gas entrance temperature between 250° and 350° C., in the illustrated example at a temperature of 300° C. at an average pressure of 37.5 bar. The gas is converted into a methane rich product gas in this last internally cooled reactor.

The change of the composition of the gas as it passes through the installation can be seen from FIG. 2. Column a, as above mentioned, gives the input composition of the synthesis gas. Column b shows the composition of the portion of the gas that has flowed through the reactor 1, that is, the composition observable at the outlet of that reactor. This portion of the gas at this location has about the following composition: 41% by volume $H_2O$, 56% by volume $CH_4$, 0.6% by volume $CO_2$, 2% by volume $H_2$, remainder nitrogen. After rejoining the remaining portion of the synthesis gas there is present at the input of the adiabatic reactor 2 a gas composition of about 25% by volume $H_2O$, 42% by volume $CH_4$, 3% by volume CO, 4% by volume $CO_2$, 26% by volume $H_2$, remainder nitrogen (tabulated in column c of FIG. 2), and at the output of the adiabatic reactor 2, after partial methanization therein, a composition of about 35% by volume $H_2O$, 52% by volume $CH_4$, 0.2% by volume CO, 3% by volume $CO_2$, 11% by volume $H_2$, remainder nitrogen (FIG. 2, column d). After passing through the second internally cooled reactor 4 there are contained in the product gas about 41% by volume $H_2O$, 57% by volume $CH_4$, 0.4% by volume $CO_2$, and 1% by volume $H_2$, the remainder nitrogen (FIG. 2, column e) and after further cooling of the product gas to 40° C. at a pressure of 36.5 bar a product gas is finally obtained that has the composition given in column f of the table of FIG. 2.

In order to utilize the residual heat in the product gas flowing out of the second internally cooled reactor at 300° C., two additional heat exchangers 21 and 22 are connected in the installation at the output of the second internally cooled reactor 4. One of these heat exchangers, the heat exchanger 21, serves for preheating of fresh water. In the illustrated example the water supplied to a water pump 23 at 50° C. and 3 bar and brought up to a pressure of 110 bar is preheated up to 160° C. In the cooling system 12 of the second internally cooled reactor, the fresh water then reaches, at the same pressure, the saturated steam temperature of 318° C.

In the heat exchanger 22 the synthesis gas flowing towards the first internally cooled reactor 1 is preheated. The synthesis gas arrives in the installation at 10° C. at a pressure of 41 bar and is heated up to 230° C. in the heat exchanger 22. In another heat exchanger 24 that as seen in the direction of flow of the gas is connected downsteam of the heat exchanger that serves for superheating the saturated steam, a further heating up of the inflow of synthesis gas to 340° C. takes place. The synthesis gas flows at this temperature through a gas cleaner 25 for desulfurization before finally a portion of this synthesis gas flow is branched off to the first internally cooled reactor 1 and then supplied along with the remainder of the synthesis gas to the adiabatic reactor 2. The gas cleaner 25 is filled with zinc oxide (ZnO) for removal of sulfur from the synthesis gas.

It is remarkable that the installation has no propelling machinery in the gas stream. The guiding of the process flow with the use of two internally cooled reactors and one adiabatic reactor is so constituted that the permissible catalyst temperature in the adiabatic reactor is not exceeded. Care is taken to assure that all of the fresh water that reaches the installation at a temperature between 40° C. and 50° C. is heated by the quantity of heat set free in the conversion of the synthesis gas in the reactor and contained in the product gas, first to the saturated steam temperature, then converted into saturated steam and finally into superheated steam. This objective can be obtained in the above described process, quite remarkably:

without addition of water vapor into the synthesis gas;

without recirculating product gas by means of compressors; and without using an external supply of heat for preheating of fresh water and of synthesis gas.

Although the invention has been described with reference to a particular illustrative example, modifications and variations are possible within the inventive concept. Thus for example instead of a single first internally cooled reactor, two or more of them may be used, in parallel and likewise two or more adiabatic reactors may be used, each with its following heat exchanger.

We claim:

1. Process for generating superheated steam in heat exchange with a synthesis gas containing carbon monoxide, carbon dioxide and hydrogen utilized for catalytic methanization comprising the steps of:

passing a part of the synthesis gas stream through at least one first internally water-cooled reactor(1);

thereafter reuniting said part of said gas stream with the remainder of said gas stream and passing the reunited gas stream in succession, through an adiabatic reactor (2), a first heat exchanger (3) and a second internally water-cooled reactor (4);

passing water, in succession, first through the cooling system of said second internally water-cooled reactor (4) for preheating thereof to a temperature approximating the saturated steam temperature, and thereafter into said at least one first internally water-cooled reactor (1) for conversion therein into saturated steam and passing said saturated steam out of the cooling system of said at least one first reactor (1) and superheating said steam in said first heat exchanger (3).

2. A process as defined in claim 1 in which after the step of passing water through the cooling system of said second internally-water-cooled reactor (4) and before supplying said water to the cooling system of said at least one first internally-water-cooled reactor (1), the heated water is passed through a steam drum (16) and from there to said at least one first reactor, and in which process the saturated steam produced in said at least one first internally-water-cooled reactor (1) is then passed through said steam drum (16) before proceeding to said first heat exchanger (3) for superheating therein.

3. Process as defined in claim 1 or claim 2 in which said water, prior to its introduction into said second internally water-cooled reactor (4) is preheated in a second heat exchanger (21) by product gas flowing out of said second internally water-cooled reactor (4).

4. Process as defined in claim 3 in which only a part of the product gas flowing out of said second internally water-cooled reactor (4) is utilized for preheating said water and the remaining portion of said product gas is utilized for preheating said synthesis gas in a third heat exchanger (22) prior to the entry of a portion of said gas into said at least one first internally water-cooled reactor (1).

5. Process as defined in claim 1 in which said synthesis gas is preheated by heat exchange with the hot gas flowing out of said adiabatic reactor (2) before said synthesis gas is introduced into said at least one first internally water-cooled reactor (1).

* * * * *